United States Patent
Stone et al.

(10) Patent No.: US 7,850,711 B1
(45) Date of Patent: Dec. 14, 2010

(54) METHOD AND APPARATUS FOR SECURING SOFT TISSUE TO BONE

(75) Inventors: Kevin T Stone, Winona Lake, IN (US);
Jason D Meridew, Syracuse, IN (US);
Troy M Walters, Plymouth, IN (US);
Ryan A Kaiser, Leesburg, IN (US);
Zachary M Hoffman, Warsaw, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 1186 days.

(21) Appl. No.: 11/159,062

(22) Filed: Jun. 22, 2005

(51) Int. Cl.
*A61B 17/04* (2006.01)

(52) U.S. Cl. .................. 606/232; 606/326; 606/327; 623/13.14

(58) Field of Classification Search ............. 606/72–73, 606/92–94, 232, 313, 320, 321, 326, 327; 623/13.13, 13.14
See application file for complete search history.

(56) References Cited

U.S. PATENT DOCUMENTS

| | | | | |
|---|---|---|---|---|
| 4,627,434 A * | 12/1986 | Murray | ..................... | 606/63 |
| 5,632,748 A | 5/1997 | Beck, Jr. et al. | | |
| 5,827,289 A | 10/1998 | Reiley et al. | | |
| 5,888,220 A | 3/1999 | Felt et al. | | |
| 5,899,938 A | 5/1999 | Sklar et al. | | |
| 5,906,632 A * | 5/1999 | Bolton | ..................... | 606/232 |
| 5,989,253 A | 11/1999 | Bigliardi | | |
| 6,056,752 A | 5/2000 | Roger | | |
| 6,099,530 A | 8/2000 | Simonian et al. | | |
| 6,110,211 A * | 8/2000 | Weiss | ..................... | 623/23.11 |
| 6,517,579 B1 | 2/2003 | Paulos et al. | | |
| 6,554,862 B2 | 4/2003 | Hays et al. | | |
| 6,632,235 B2 | 10/2003 | Weikel et al. | | |
| 6,635,063 B1 * | 10/2003 | Litwin et al. | ................. | 606/104 |
| 6,726,691 B2 * | 4/2004 | Osorio et al. | ................. | 606/94 |
| 7,572,283 B1 * | 8/2009 | Meridew | ..................... | 606/321 |
| 2002/0026195 A1 * | 2/2002 | Layne et al. | ................. | 606/72 |
| 2003/0135274 A1 | 7/2003 | Hays et al. | | |
| 2003/0144735 A1 | 7/2003 | Sklar et al. | | |
| 2003/0176865 A1 | 9/2003 | Supinski | | |
| 2004/0210297 A1 * | 10/2004 | Lin et al. | ..................... | 623/1.11 |
| 2004/0220615 A1 | 11/2004 | Lin et al. | | |
| 2005/0182417 A1 * | 8/2005 | Pagano | ..................... | 606/92 |

FOREIGN PATENT DOCUMENTS

WO   WO-2005032326   4/2005

* cited by examiner

*Primary Examiner*—Thomas C Barrett
*Assistant Examiner*—Michael J Araj
(74) *Attorney, Agent, or Firm*—Harness, Dickey

(57) ABSTRACT

A system and method to assist in securing a soft tissue replacement in a bone tunnel includes an expandable member having an opening and an expandable portion. A delivery structure includes a connection portion selectively coupled to the opening of the expandable member. The delivery structure is adapted to inject a flowable medium into the expandable member thereby expanding the expandable portion and urging the soft tissue replacement into a bone surface defining the bone tunnel.

21 Claims, 12 Drawing Sheets

METHOD AND APPARATUS FOR SECURING SOFT TISSUE TO BONE

FIELD OF THE INVENTION

The present invention relates to endoscopic soft tissue fixation. More particularly, the present invention relates to an apparatus and a method for securing soft tissue within a bone tunnel.

INTRODUCTION

Ligaments and tendons are soft collagenous tissues. Ligaments are strong fibrous connective soft tissue which connects the articular ends of bones to bind them together and to facilitate or limit motion. Tendons connect muscle to bone. Injuries to ligaments are common, and patients who are physically active are generally more susceptible to such ligament injuries. The anterior cruciate ligament (ACL) of the knee joint is a ligament frequently injured by such patients. Such injuries cause instability in the knee joint which, when left untreated, may lead to degenerative arthritis. Because of this condition, ACL reconstruction may be required. Generally during ACL reconstruction, a substitute soft tissue ligament or graft is attached to the femur and/or tibia to facilitate regrowth and permanent attachment.

One method of performing this reconstruction involves the use of a section of bone-patellar tendon-bone as a graft. With this method, a ligament tunnel is bored into both the femur and the tibia and the bone-patellar tendon-bone graft is centered between the tunnel. The bone portions of the graft are then each secured within the respective tunnels by tightening an interference screw in each tunnel between the bone graft and the side of the tunnel.

However, use of such a technique may present several disadvantages. For example, the graft may be inadvertently cut or frayed by the sharp edges of the interference screw during insertion of the screw and subsequent to fixation. Moreover, if the interference screw or the bone graft is slightly oversized versus the size of the tunnel, the interference screw may cause too much force to be exerted on the bone graft portion as the interference screw is tightened. This may subsequently cause the bone graft portion to be damaged and not useable. In addition, it may be difficult to accurately gauge the length of the bone-patellar tendon-bone graft in relation to the ligament tunnels such that the bone graft portions may not seat appropriately within the tunnels or be properly tensioned.

Another method for performing this reconstruction involves the use of only a soft tissue ligament graft. Such a graft is generally taken from the hamstring ligament, specifically, the semitendinosus and gracilis ligaments or tendons. Such grafts are generally fed through the ligament tunnel and secured outside the tunnel. The graft is generally secured by a non-endoscopic means of stapling or screwing the graft onto the outside surface of the tibia and/or femur.

However, this method of securing the soft tissue graft may also exhibits disadvantages. For example, if the graft has been taken from the patient (autograft), the harvest site of the graft leads to longer recovery. If an allograft is desired, availability may be low. In addition, since the various staple or screw and washer assemblies in existence are positioned on the outside of the bone surface or extend beyond the bone surface, such components may be noticed by the patient and in some instances may cause patient discomfort. In addition, because of the discomfort, it may be required to perform subsequent surgery to remove the staple or screw and washer assembly once the graft has permanently attached to the bone, thereby subjecting the patent to a second surgery, as well as increasing overall surgical costs. The staple or screw and washer assembly may not be substantially resistant to slippage and may not provide stiff securement. In other words, the graft may permanently slip under the securement of the staple or screw and washer assembly thereby providing a non-optimum tension on the graft. Securement at the anchoring point may also be resilient such that if the graft utilizes sutures in combination with the staple or screw washer assembly, the anchoring point may stretch under stress and resiliently return, thereby also providing non-optimum tensioning or stiffness for the graft.

SUMMARY

A system and method to assist in securing a soft tissue replacement in a bone tunnel includes an expandable member having an opening and an expandable portion. A delivery structure includes a connection portion selectively coupled to the opening of the expandable member. The delivery structure is adapted to inject a flowable medium into the expandable member thereby expanding the expandable portion and urging the soft tissue replacement into a bone surface defining the bone tunnel.

In various embodiments, the expandable member may comprise an impermeable membrane or alternatively a porous material. The expandable member may be resorbable. The flowable medium may comprise air, bone cement, or any other biocompatible material.

In other various embodiments, the system may further comprise a bone screw operable to be advanced into the bone tunnel and thereby compress the soft tissue replacement into the bone surface. The bone screw may be operable to compress the soft tissue replacement into the bone surface and pass the flowable medium through a passage in the bone screw subsequent to compressing the soft tissue replacement into the bone surface.

In other various embodiments, a system to assist in securing a soft tissue replacement in a bone tunnel includes a longitudinal sleeve member. A pin member extends through the sleeve member and includes a distal end attached to the sleeve member and a proximal end extending from the sleeve member. The pin is selectively movable from an install position to an expand position wherein the pin member causes the longitudinal member to expand outwardly thereby urging the soft tissue replacement into a bone surface defining the bone tunnel.

According to other various embodiments the sleeve member is deformable. The sleeve member defines slots and wherein the slots define openings when the pin member is moved to the expanded position. The system may further include a delivery structure selectively coupled to an opening on the longitudinal member. The delivery structure is adapted to inject a flowable medium into the opening on the longitudinal sleeve member. The slots are adapted to pass the flowable medium into the bone surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION OF VARIOUS EMBODIMENTS

Figure 1:
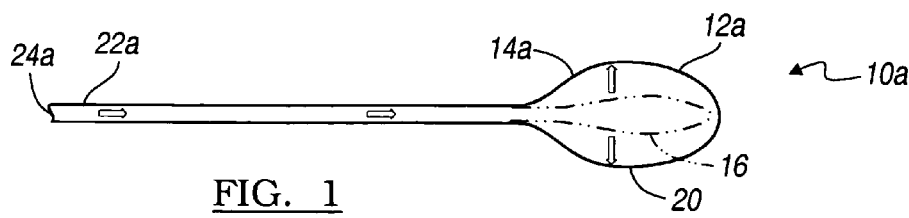
FIG. 1 is a plan view of an apparatus to assist in securing a soft tissue replacement in a bone tunnel according to the present teachings.

The following description of the embodiment(s) is merely exemplary in nature and is in no way intended to limit the invention, its application, or uses. Moreover, while the present teachings are discussed in detail below with regard to ACL reconstruction, those skilled in the art will recognize the other types of soft tissue fixation may employ the present teachings.

With initial reference to FIGS. 1-4C, a plurality of tendon fixation devices 10a-10d according to the present teachings are illustrated. The fixation devices 10a and 10b illustrated in FIGS. 1 and 2 generally define expandable members 12a and 12b. The expandable member 12a is an impermeable membrane and includes a distal end portion 14a adapted to expand from a generally narrow contour 16 to a generally bulbous contour 20. A proximal end portion 22a of the expandable member 12a defines an opening 24a. As will be described in greater detail below, the expandable member 12a is adapted to accept a flowable medium through the opening 24a thereby expanding the distal end portion 14a from the narrow contour 16 to the bulbous contour 20.

Figure 2:
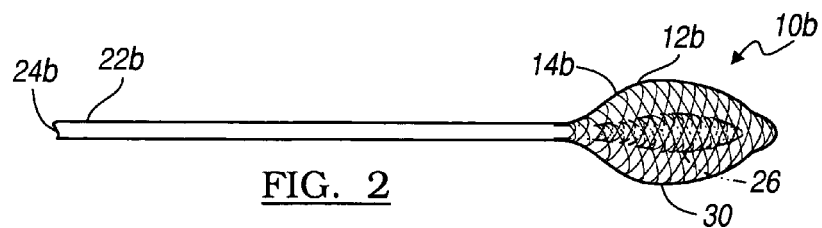
FIG. 2 is a plan view of an apparatus to assist in securing a soft tissue replacement in a bone tunnel according to additional features.

The expandable member 12b illustrated in FIG. 2 includes a distal end portion 14b adapted to expand from a generally narrow contour 26 to a generally bulbous contour 30. The distal end portion 14b defines a porous membrane. A proximal end portion 22b of the expandable member 12b defines an opening 24b. As will be described, the expandable member 12b is adapted to accept a flowable medium through the opening 24b thereby expanding the distal end portion 14b. The porous material is adapted to pass the flowable medium from the expandable member 12b and into bone surface defining a bone tunnel. The expandable members 12a and 12b may be made of a polyglycolic acid (PGA), polylactic acid (PLA) polymer such as LactoSorb® manufactured by Biomet, Inc., of Warsaw, Ind.

Figure 3A:
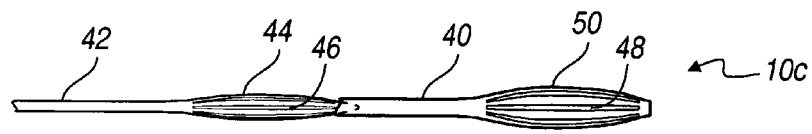
FIG. 3A is a plan view of an apparatus including an inner portion and an outer portion to assist in securing a soft tissue replacement in a bone tunnel according to additional features.
Figure 3B:
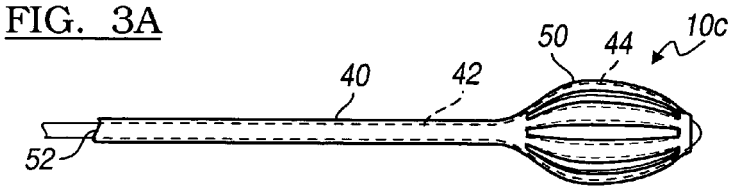
FIG. 3B is a plan view of the apparatus of FIG. 3A shown with a distal portion in an expanded position.

The fixation device 10c illustrated in FIGS. 3A and 3B includes an outer tube member 40 and an inner tube member 42. The inner tube member 42 includes a distal end portion 44 defining a plurality of slots 46. Similarly, the outer tube member 40 defines a plurality of slots 48 arranged on a distal end 50. As will be described in further detail below, during operation, the inner tube member 42 is adapted to insert through a proximal opening 52 (FIG. 3B) in the outer tube member 40. Once the distal end portion 44 of the inner tube member 42 aligns with the distal end portion 50 of the outer tube member 40 (FIG. 3B), a flowable medium is injected into the inner tube member 42. The flowable medium causes the distal end portion 44 of the inner tube member 42 to expand. As a result, the distal end portion 50 of the outer tube member 40 expands. The flowable medium flows from the inner tube member 42 through the plurality of slots 46 formed on the inner tube member 42 and out the plurality of slots 48 formed on the outer tube member 40. As will be described below, the outer tube member 40 (and flowable medium) urges soft tissue replacement into the bone surface defining a bone tunnel.

Figure 4A:
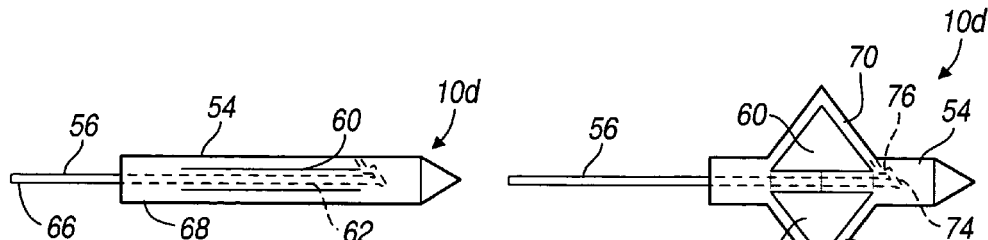
FIG. 4A is a plan view of an apparatus to assist in securing a soft tissue replacement in a bone tunnel according to additional features and shown in an insertion position.
Figure 4B:
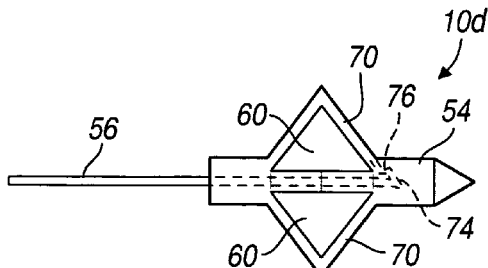
FIG. 4B is a plan view of the apparatus of FIG. 4A shown in an expanded position.
Figure 4C:
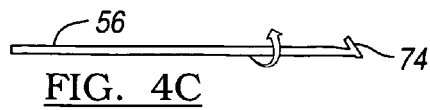
FIG. 4C is a plan view of a shaft portion of the apparatus of FIG. 4B shown rotated and removed from the apparatus.

Turning now to FIGS. 4A-4C, the fixation device 10d is illustrated. The fixation device 10d generally includes a longitudinal sleeve member 54 and a pin member 56. The sleeve member 54 defines a plurality of slots 60 formed thereon. The pin member 56 includes a distal end 62 selectively attached to the sleeve member 54 at a retaining portion 76 and a proximal end 66 extending from a proximal end 68 of the sleeve member 54. The fixation device 10d is selectively movable from an insertion position (FIG. 4A) to an expanded position (FIG. 4B). The pin member 56 is operable to be linearly translated from the insertion position, in a direction away from the sleeve member 54 to the install position. During linear translation of the pin member 56, the operator may hold a proximal portion of the sleeve member 54 in a static position. Translation of the pin member 56 relative the sleeve member 54 (in a direction leftward as illustrated in FIG. 4B) causes the sleeve member 54 to expand outwardly. Portions of the sleeve member 54 between adjacent slots 60 expand outwardly to define a plurality of wing portions 70 in the expanded position. The sleeve member 54 may be made of a PGA/PLA polymer such as LactoSorb® or other suitable biocompatible material.

Once the fixation device 10d is moved to the expanded position, the pin member 56 may be retracted from the sleeve member 54 (FIG. 4C). In one implementation, the pin member 56 may be rotated about its axis causing a hook portion 74 formed on its distal end to disengage a retaining portion 76 incorporated on an inner dimension of the sleeve 54. Once the hook portion 74 clears the retaining portion 76 of the sleeve member 54, the pin 56 may be retracted from the sleeve 54 (in a direction leftward as illustrated in FIG. 4B).

Figure 5:
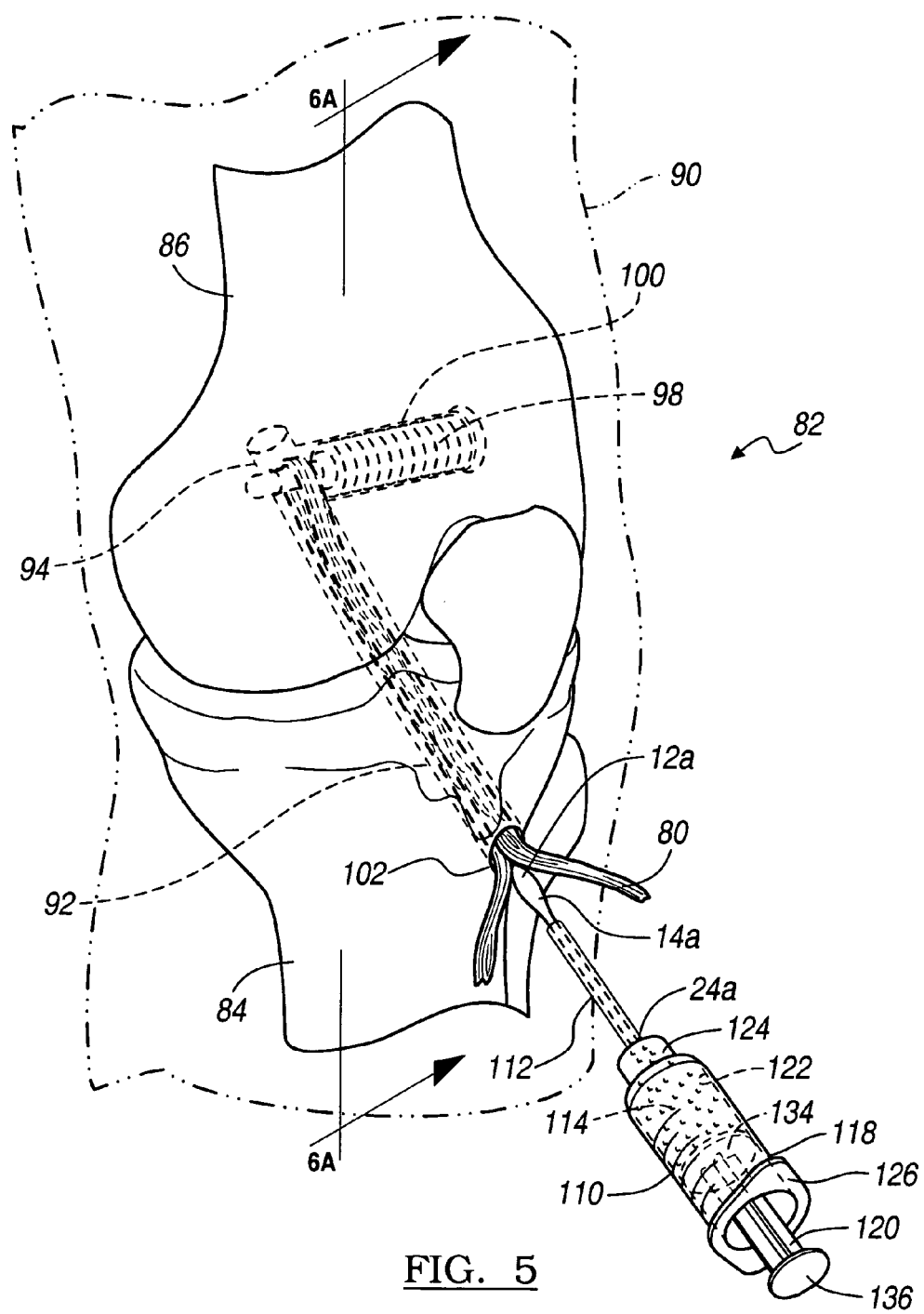
FIG. 5 is a perspective view of the apparatus of FIG. 1 attached to a delivery device and implanted through a tibial tunnel between strands of the soft tissue replacement.
Figure 6A:
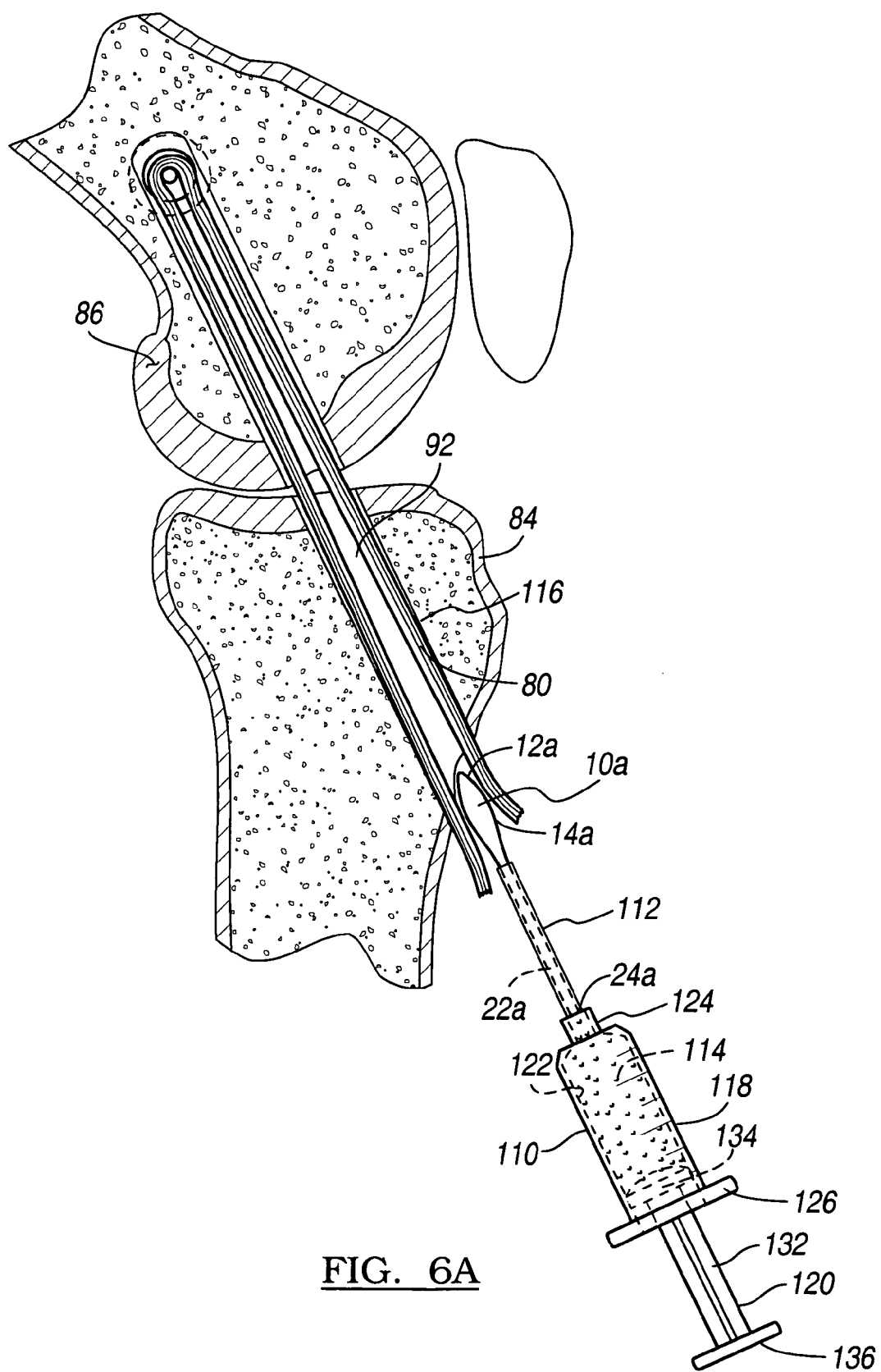
FIG. 6A is a sectional view of the apparatus of FIG. 5 taken along line 6A-6A.
Figure 6B:
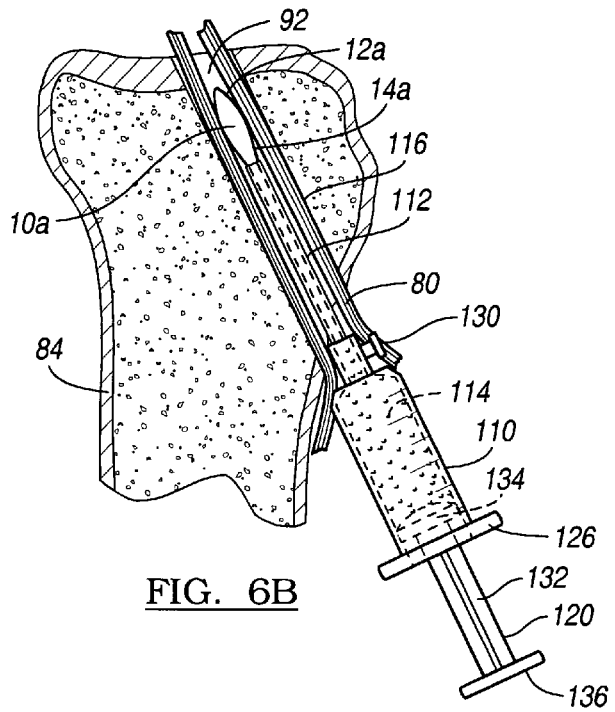
FIG. 6B is a sectional view of the apparatus of FIG. 6A shown in an insertion position implanted into the tibial tunnel.
Figure 6C:
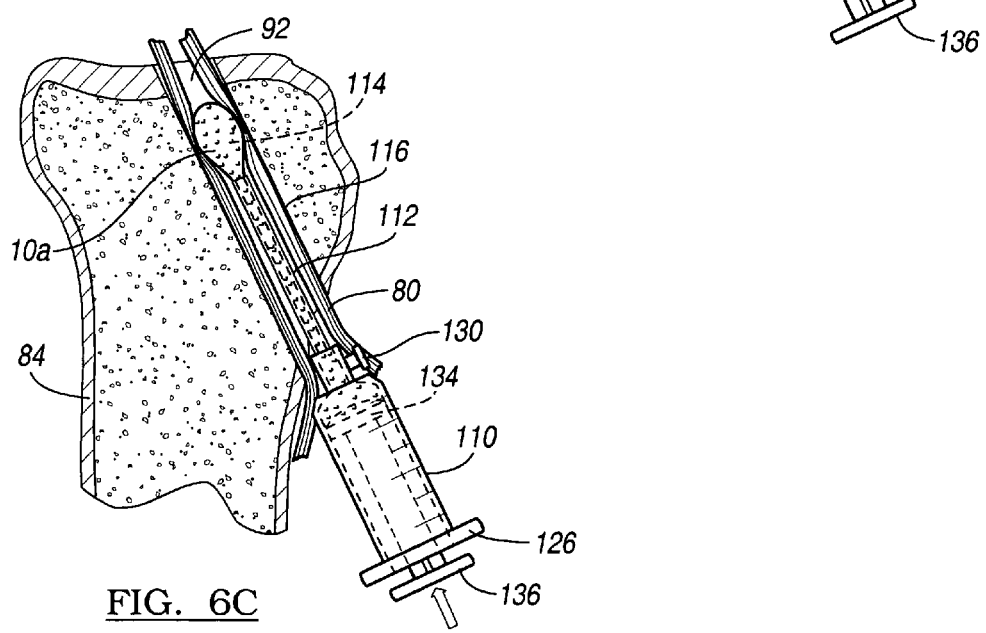
FIG. 6C is a sectional view of the apparatus of FIG. 6B shown in an expanded position implanted into the tibial tunnel.
Figure 6D:
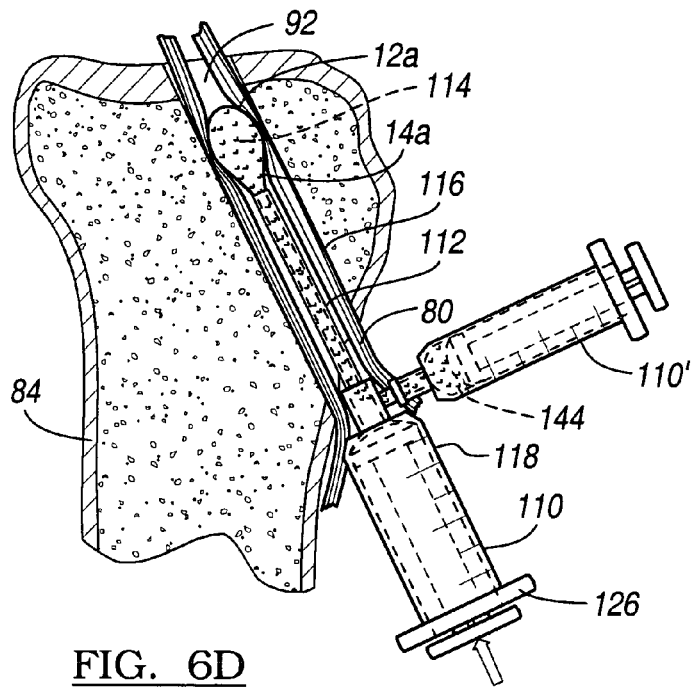
FIG. 6D is a sectional view of the apparatus of FIG. 6C shown with a secondary delivery device according to additional features.
Figure 6E:
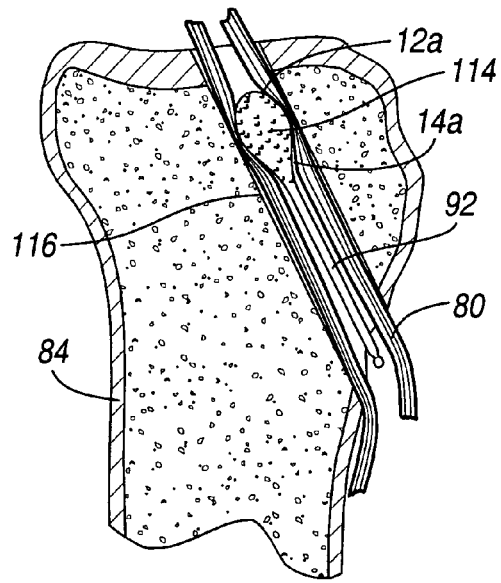
FIG. 6E is a sectional view of the apparatus of FIG. 6C shown with the delivery device removed.

With reference now to FIGS. 5-6E, a method for securing a soft tissue replacement 80 according to a first implementation will be described. With particular reference to FIGS. 5 and 6A, a knee 82 generally includes at least a tibia 84 and a femur 86 surrounded by soft tissue 90. The knee 82 is initially prepared by forming a tibial tunnel 92 and a femoral tunnel 94. It is understood that incisions must first be made in the soft tissue 90 surrounding the tibia 84 such that a tool may engage the tibia 84 and the femur 86 to form the tibial tunnel 92 and the femoral tunnel 94.

The soft tissue replacement 80 extends through the tibial tunnel 92 and the femoral tunnel 94. As shown, a soft tissue replacement 80 is supported around a crosspin 98 implanted in a transverse femoral tunnel 100. Free ends of the replacement tissue 80 extend through an opening 102 of the tibial tunnel 92. The following description is directed to securing portions of the soft tissue replacement 80 into the bone wall of the tibial tunnel 92 during ACL reconstruction. It is appreciated that the attachment method of the soft tissue replacement 80 to the femur 86 (such as by way of the crosspin 98) is merely exemplary and that other methods may be employed. Furthermore, while the particular implementations illustrated herein are directed toward securing a replacement tissue within a tibial tunnel, the same may be applied to securing other replacement tissues to other bone tunnels.

As illustrated in FIGS. 5-6C, a delivery structure 110 is shown cooperating with a cannulated shaft 112 and attached to the opening 24a of the expandable member 12a. The delivery structure 110 is adapted to inject a flowable medium 114 into the distal end portion 14a of the expandable member 12a to urge the distal end portion 14a to expand into bone surface 116 (FIG. 6A) of the bone tunnel 92. The cannulated shaft 112 provides stiffness to the expandable member 12a during insertion into the bone tunnel 92. It is appreciated that other arrangements may be provided to assist in locating the expandable member 12a into the bone tunnel 92.

The delivery structure 110 may generally include a syringe portion 118 and a plunger portion 120. The syringe portion 118 includes an inner cavity 122, a distal delivery end 124 and a proximal gripping end 126. The gripping end 126 defines a radial flange. In one implementation the syringe portion 118 may optionally include a secondary injection port 130 (FIGS. 6B-6D). The plunger 120 generally includes an intermediate shaft 132 extending between an inner disk portion 134 and an outer actuation portion 136.

During operation, the distal delivery end 124 of the syringe portion 118 is connected to the opening 24a on the proximal end 22a of the expandable member 12a. Next, the expandable member 12a is located into the tibial tunnel 92 positioning the tissue replacement 80 intermediate the expandable member 12a and the bone surface 116 (FIG. 6B). The plunger 120 is then actuated causing the flowable medium 114 to be passed from the cavity 122 of the syringe 118 into the distal end portion 14a of the expandable member 12a (FIG. 6C).

Expansion of the expandable member 12a causes the soft tissue replacement 80 to be urged into the bone surface 116 of the tibial tunnel 92 to facilitate fixation of the soft tissue replacement 80 into the bone surface 116. The flowable medium 114 may comprise a flowable biologic material such as bone cement for example. It is appreciated that other materials may be similarly employed. In one implementation the expandable member may comprise a resorbable material. Once the resorbable material has been resorbed, the bone cement contacts the soft tissue replacement 80 and maintains the soft tissue replacement in an engaged position with the bone surface 116.

As illustrated in FIG. 6D, a secondary flowable medium 144 may be additionally or alternatively injected through the secondary port 130 on the syringe portion 118 by an additional delivery structure 110'. The additional delivery structure 110' may be constructed similar to the delivery structure 110. The secondary flowable medium 144 may comprise a biologic material such as bone cement. In this configuration, the expandable member 12a may initially be injected with a first flowable medium such as bone cement, air, demineralized bone matrix (DBM), hydroxyapatite (HA), or other flowable medium by the delivery structure 110' and subsequently be injected with the secondary flowable medium 144. As illustrated in FIG. 6E, the delivery structure 110 is shown removed from the expandable member 12a. In one example a portion of the expandable member 12a such as the proximal end 22a may be tied or otherwise clamped upon removal of the delivery structure 110. Depending on the specific application and the material properties of the flowable medium, it may be necessary to wait a predetermined amount of time before removing the delivery structure 110 from the expandable member 12a to allow the flowable material to set and/or verify the desired location of soft tissue replacement 80.

Figure 7A:
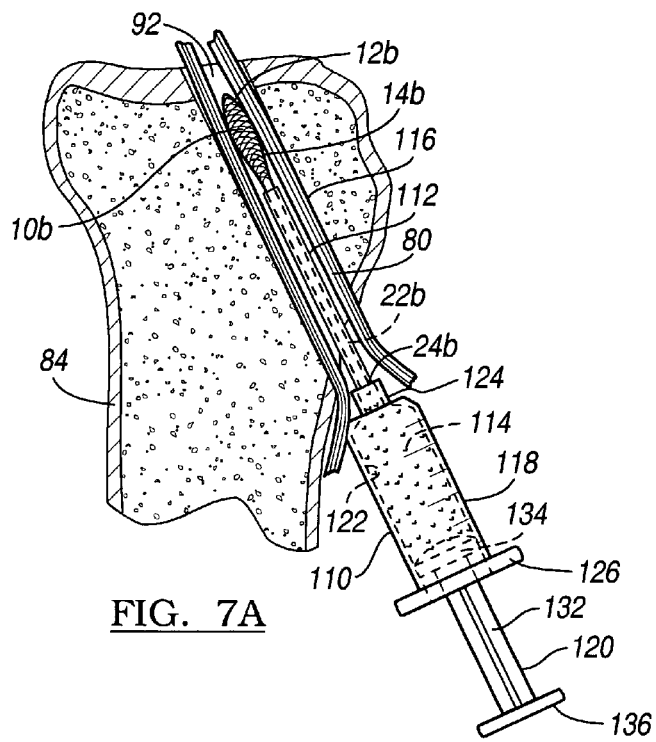
FIG. 7A is a sectional view of the apparatus of FIG. 2 shown attached to a delivery device and implanted through a tibial tunnel between strands of the soft tissue replacement.
Figure 7B:
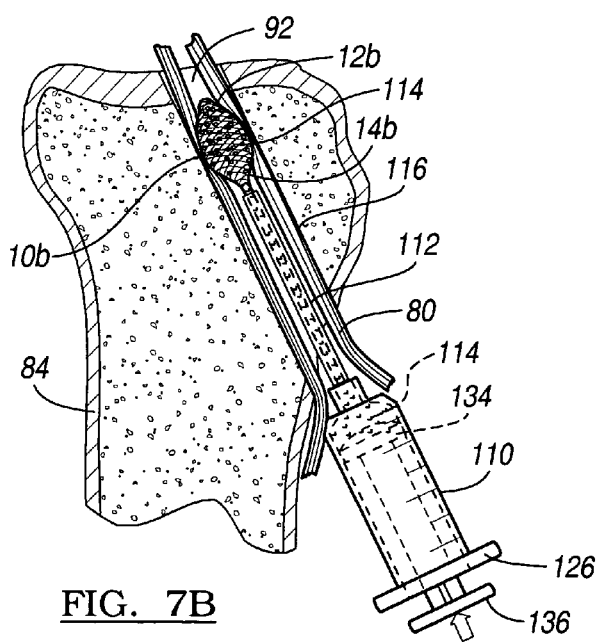
FIG. 7B is a sectional view of the apparatus of FIG. 7A shown in an expanded position implanted into the tibial tunnel.
Figure 7C:
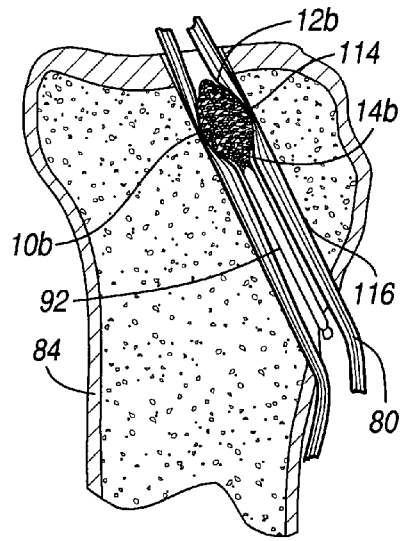
FIG. 7C is a sectional view of the apparatus of FIG. 7A shown with the delivery device removed.

Turning now to FIGS. 7A-7C, the fixation device 10b of FIG. 2 is shown during operation. At the outset the expandable member 12b is inserted into the tibial tunnel 92 such that the soft tissue replacement 80 is operatively positional between the expandable member 12b and the bone surface 116 of the tibial tunnel 92. The distal delivery end 124 of the syringe portion 118 is connected to the opening 24b on the proximal end 22b of the expandable member 12b.

Next, the flowable medium 114 is injected into the expandable member (FIG. 7B). Expansion of the distal end portion 14b of the expandable member 12b urges the soft tissue replacement 80 into the bone surface 116 of the tibial tunnel 92. The porous material of the expandable member 12b may comprise a mesh fabric material or any suitable porous biocompatible material. The porous biocompatible material allows the flowable medium to seep through the distal end portion 14b and directly into the soft tissue replacement 80 and the bone surface 116. Once the expandable member 12b is expanded to the desired position, the delivery device 110 is removed (FIG. 7C). In one example a portion of the expandable member 12ab such as the proximal end 22b may be tied or otherwise clamped upon removal of the delivery structure 110.

Figure 8A:
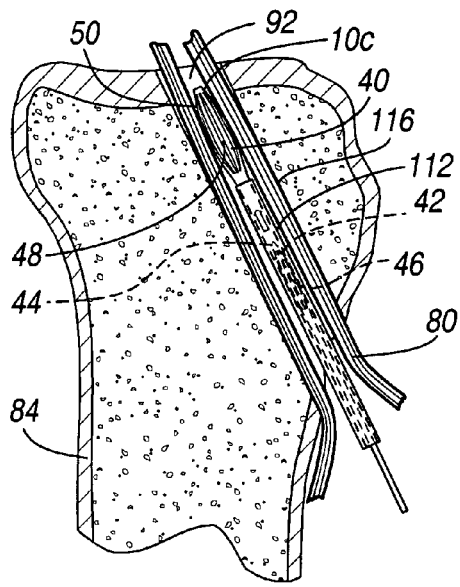
FIG. 8A is a sectional view of the apparatus of FIGS. 3A and 3B shown with the inner portion being inserted into the outer portion.
Figure 8B:
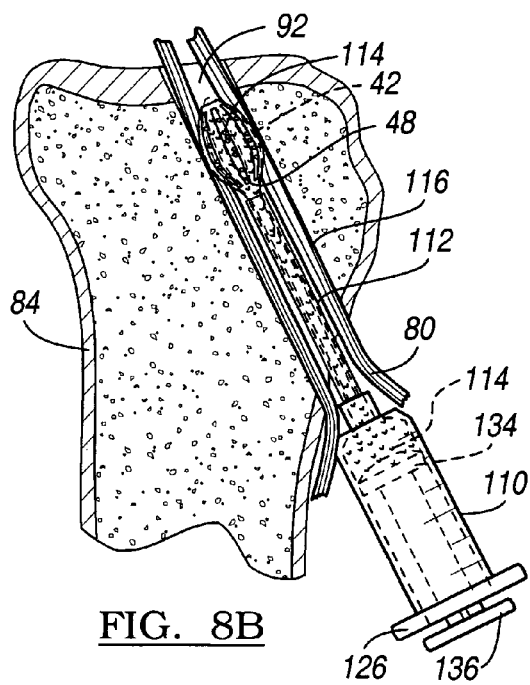
FIG. 8B is a sectional view of the apparatus of FIG. 8A shown with the outer portion in an expanded position and implanted into the tibial tunnel.
Figure 8C:
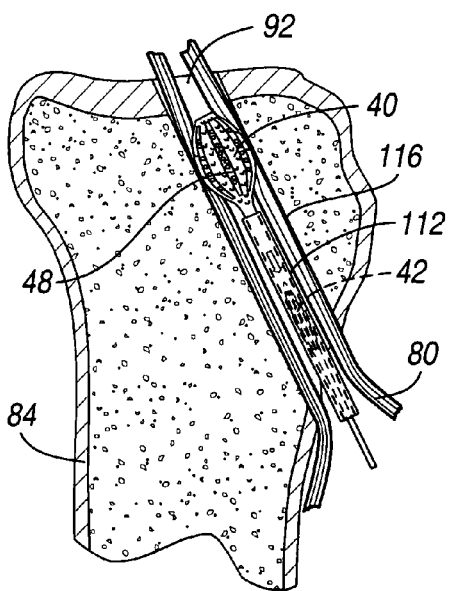
FIG. 8C is a sectional view of the apparatus of FIG. 8B shown with the inner portion being retracted from the outer portion.

With reference now to FIGS. 8A-8C, operation of the fixation device 10c illustrated in FIGS. 3A and 3B will be described in greater detail. At the outset, the outer tube member 40 is located within the bone tunnel 92. As depicted in FIG. 8A, the soft tissue replacement 80 is located intermediate the outer tube member 40 and the bone surface 116 of the tibial tunnel 92. Next, the inner tube member 42 is inserted into the outer tube member 40 until the respective distal portions 44 and 50 are aligned (FIGS. 3B and 8B). Biologic material 114 is injected into the inner tube 42 (such as by way of the delivery device 110 described herein). The biologic material 114 passes through the slots 46 and 48 (see e.g. FIG. 3A) defined in the inner and outer distal portions 44 and 50 respectively. As a result, the outer tube member 40 and the biologic material urge the tissue replacement 80 into the bone walls 116.

Figure 9A:
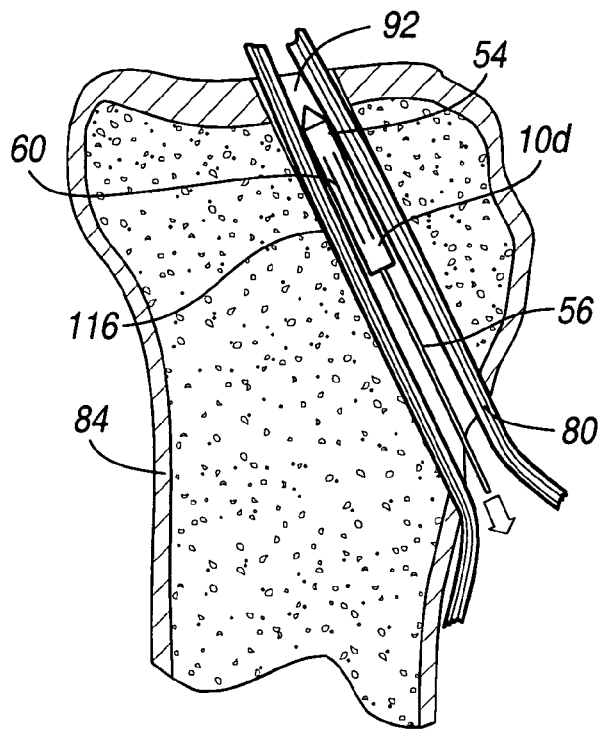
FIG. 9A is a sectional view of the apparatus of FIG. 4A shown in an insertion position and implanted through a tibial tunnel between strands of the soft tissue replacement.
Figure 9B:
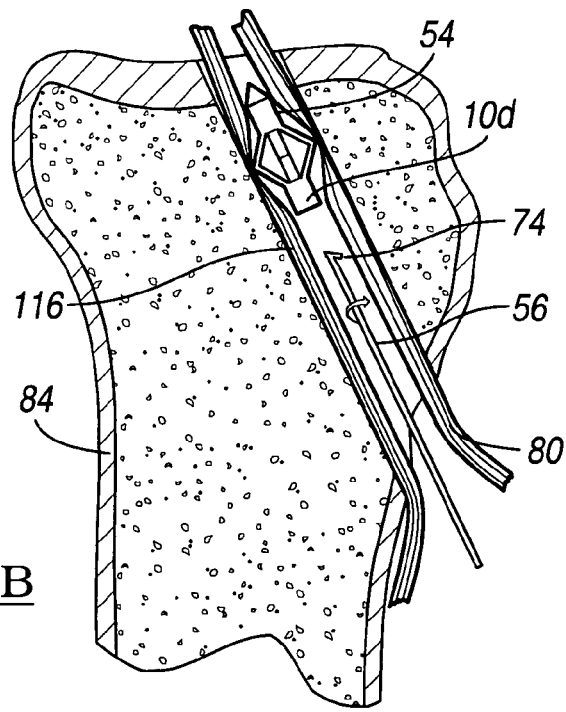
FIG. 9B is a sectional view of the apparatus of FIG. 9A shown in an expanded position and the shaft portion being removed.
Figure 9C:
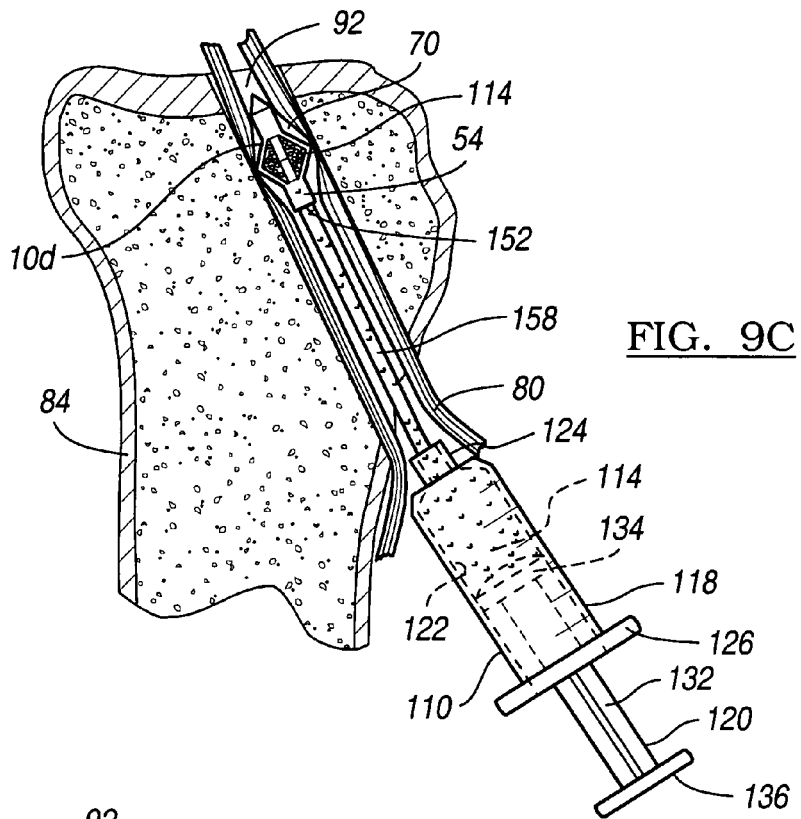
FIG. 9C is a sectional view of the apparatus of FIG. 9B shown with a delivery device attached and delivering a flowable material according to additional features.
Figure 9D:
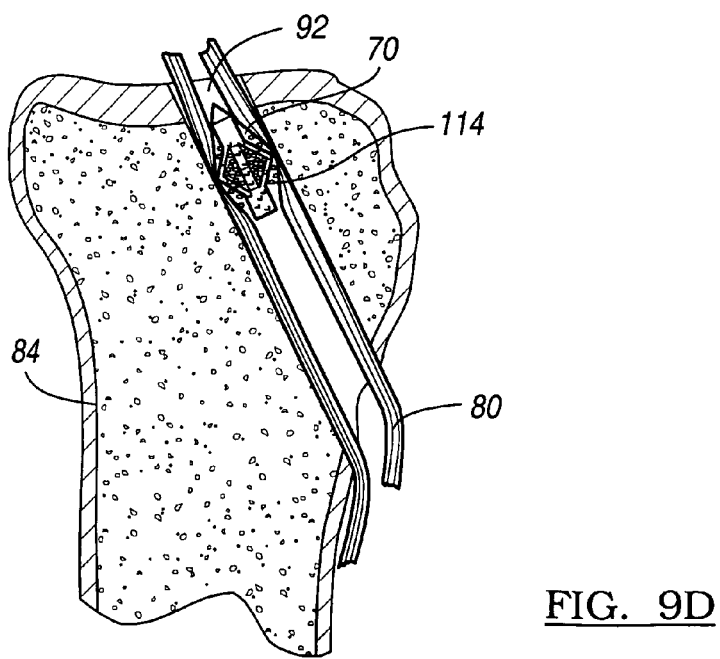
FIG. 9D is a sectional view of the apparatus of FIG. 9C shown with the delivery device removed.

Turning now to FIGS. 9A-9D, operation of the fixation device 10d illustrated in FIGS. 4A-4C will be described in greater detail. At the outset, the fixation device 10d is inserted into the tibial tunnel 92 thereby locating the replacement tissue 80 intermediate the sleeve 54 and the bone surface 116 of the tibial tunnel 92. Next, the pin member 56 is translated in a direction away from the sleeve 54 causing the sleeve 54 to expand forming the wing portions 70 (FIG. 9B). As a result, the wing portions 70 urge the tissue replacement 80 into the bone walls 116. Once the wing portions 70 are expanded, the pin member 56 is removed from the sleeve 54 (FIG. 9B). As explained with regard to FIGS. 4A-4C, the pin member 56 may have a hook 74 that may disengage a retaining ridge 76 upon rotation of the pin 56. It is appreciated that other arrangements may be provided. In one implementation, biologic material 114 may be additionally inserted through a passage 152 formed on a proximal end 68 of the sleeve 54. More specifically, as illustrated in FIGS. 9C and 9D, a cannulated extension shaft 158 may be coupled between the sleeve member 54 and the delivery structure 110. Depression of the plunger 120 causes the biologic material 114 to flow from the cavity 122 of the syringe 118 through the cannulated extension shaft 158 and into the sleeve 54 of the fixation device 10d.

Figure 10:
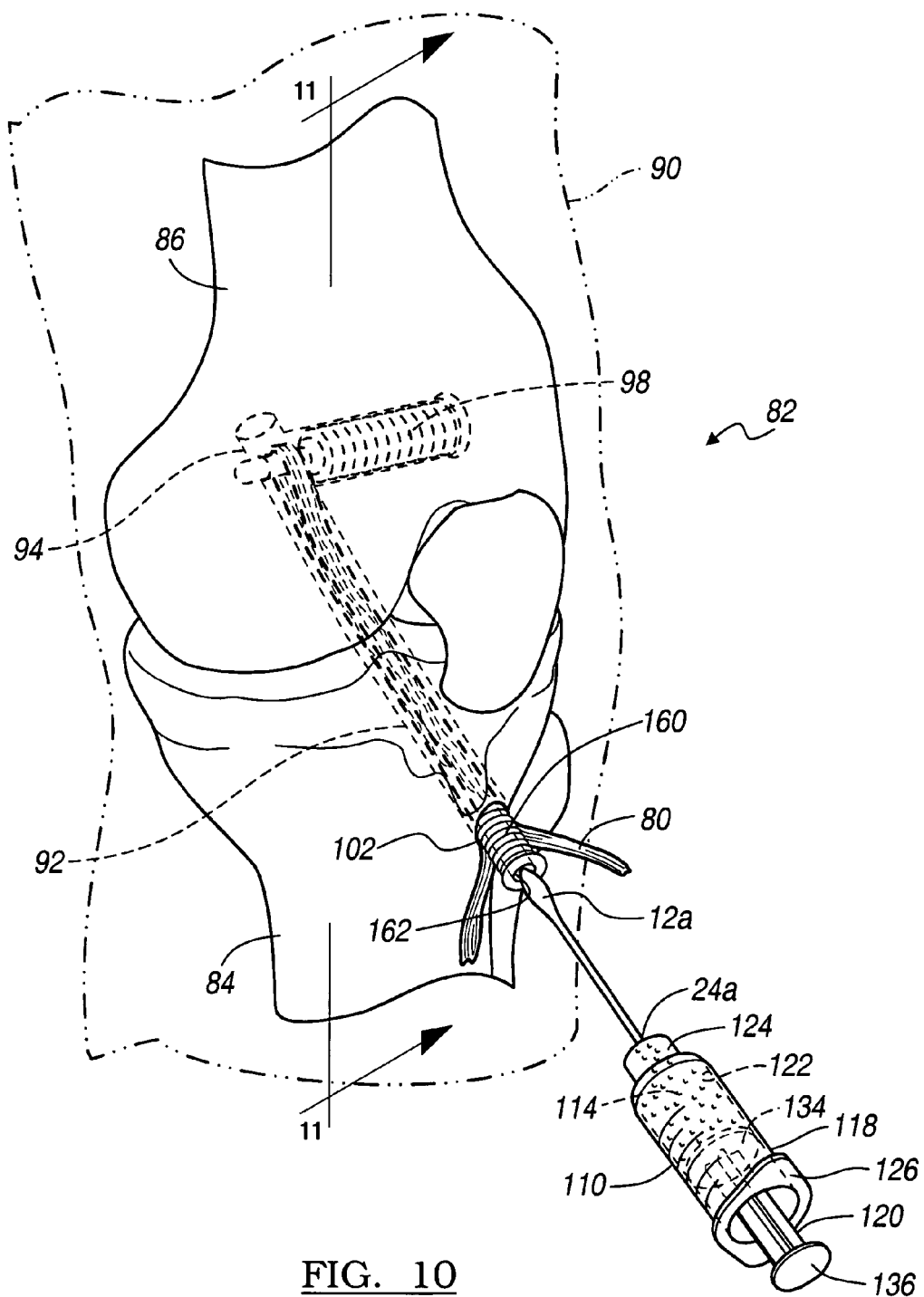
FIG. 10 is a perspective view of the apparatus of FIG. 1 attached to a delivery device and implanted through a cannulated portion of a complementary securing member and into the tibial tunnel between strands of the soft tissue replacement.
Figure 11:
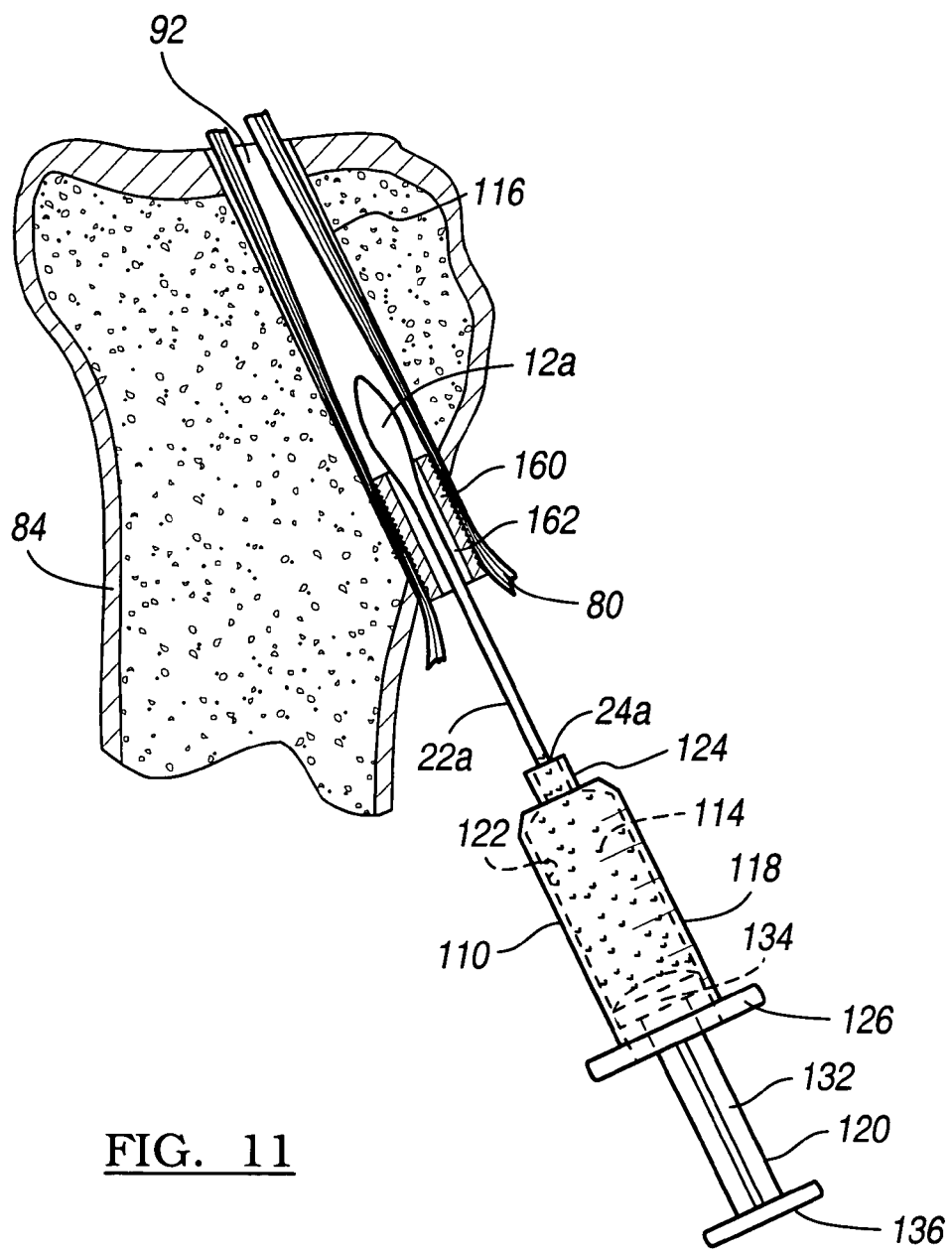
FIG. 11 is a sectional view of the apparatus and complementary securing member of FIG. 10 taken along line 11-11.

Turning now to FIGS. 10 and 11, a fixation method according to additional features will be described. In general, the fixation method according to FIGS. 10 and 11 utilizes the expandable member 12a (or 12b) described herein as part of a secondary or supplemental fixation device. Explained further, the expandable member 12a is used in combination with a complementary fixation member such as a cannulated bone screw 160. In this method, the tissue replacement 80 may be initially fixed to the bone surface 116 of the tibial tunnel 92 by the cannulated bone screw 160. Once the soft tissue replacement 80 is urged into the bone surface 116 and stabilized by the cannulated bone screw 160, the expandable member 12a may be disposed through cannulated portion 162 of the bone screw 160 and expanded according to the techniques described herein. Such a system is particularly useful in temporarily stabilizing and tensioning the soft tissue replacement 80 within the bone tunnel 92 while the expandable member 12a is expanded into a desired position. It is appreciated that the cannulated bone screw 160 may be a standalone component or alternatively a portion of a fixation component. It is also appreciated that any of the fixation devices and methods explained herein may be utilized with a complementary or secondary device such as the cannulated bone screw 160.

Figure 12A:
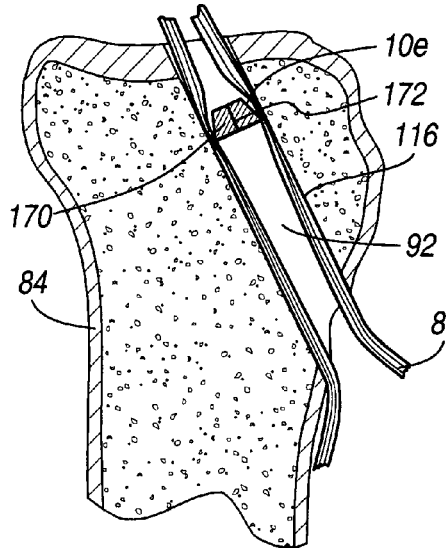
FIG. 12A is a sectional view of an apparatus to assist in securing a soft tissue replacement in a bone tunnel according to additional features.
Figure 12B:
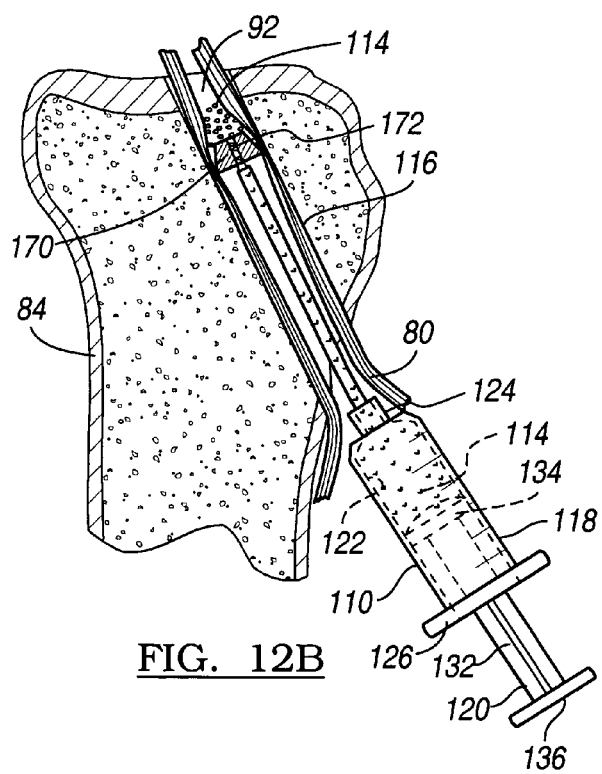
FIG. 12B is a sectional view of the apparatus of FIG. 12A shown with a delivery device delivering a flowable material through a central passage of the apparatus.
Figure 12C:
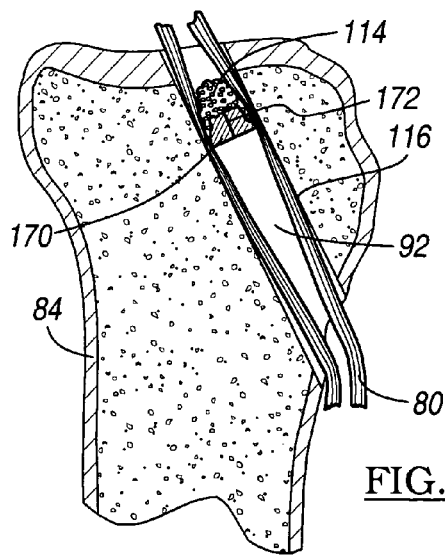
FIG. 12C is a sectional vie of the apparatus of FIG. 12B shown with the delivery device removed.

With reference now to FIGS. 12A-12C, a fixation device 10e according to additional features is shown. The fixation device 10e generally comprises a tapered body portion 170 having a sealable central passage 172. During operation, the fixation device 10e is implanted into the bone tunnel 92 thereby urging the soft tissue replacement 80 into contact with the bone surface 116 of the bone tunnel 92 (FIG. 12A). Once the fixation device 10e is located into the desired position, biologic material 114 is injected (such as by way of the delivery device 110 described herein) through the central passage 172 and to a location inboard the tapered body portion 170 (FIG. 12B). Once the desired amount of biologic material 114 has been inserted to a location beyond the fixation device 10e, the central passage 172 closes thereby capturing the biologic material 114 at the inboard location (FIG. 12C). Explained further, the surrounding material of the central passage 172 expands when outward pressure is applied and retracts to a closed, sealed position when pressure is relieved. In one implementation, once the biologic material 114 has cured a desired amount, the fixation device 10e may be removed from the tibial tunnel. In another implementation, the fixation device 10e may be resorbable and remain in the bone tunnel 92.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, the specification and the following claims.

What is claimed is:

1. A method for securing a soft tissue replacement in a bone tunnel comprising:
    forming a tunnel in a bone;
    locating the soft tissue replacement in the tunnel;
    passing a first tube member through an opening in the tunnel whereby the soft tissue replacement locates between the first tube member and
a bone surface defining the tunnel;
    passing a second tube member into the first tube member; and
    injecting a flowable medium into the second tube member wherein the flowable medium passes through respective openings defined on the first and second tube members respectively and urging the flowable medium against the soft tissue replacement and into contact with the bone surface.

2. The method of claim 1 wherein passing the second tube member includes inserting the second tube member into the first tube member until respective distal portions on the first and second tubes are aligned.

3. The method of claim 1 wherein forming said tunnel includes forming said tunnel having an entrance and wherein locating said soft tissue replacement includes passing at least a portion of said soft tissue replacement through said entrance.

4. The method of claim 3 wherein locating said soft tissue replacement further includes locating a portion of said soft tissue replacement at a location that extends out of said entrance during said urging of said soft tissue replacement into contact with said bone.

5. A method for securing a soft tissue replacement in a bone tunnel comprising:
forming a tunnel in a bone;
locating the soft tissue replacement in said tunnel;
passing an expandable member into said tunnel, whereby the soft tissue replacement locates between said expandable member and a bone surface defining said tunnel, wherein said expandable member includes a sleeve member and a pin member extending through said sleeve member, said pin member having a distal end attached to said sleeve member and a proximal end extending from said sleeve member; and
expanding said expandable member thereby urging said soft tissue replacement into contact with said bone surface, wherein expanding said expandable member includes translating said pin member relative to said sleeve member wherein said sleeve member expands outwardly as a result of said translation thereby urging the soft tissue replacement into the bone tunnel.

6. The method of claim 5, further comprising:
rotating said pin member relative to a longitudinal axis of said sleeve member; and
removing said pin member from said sleeve member.

7. The method of claim 6 wherein rotating said pin member comprises rotating a hook portion extending from said distal end of said pin member from an engaged position with said sleeve member into a disengaged position from said sleeve member.

8. The method of claim 5 wherein expanding said expandable member comprises:
expanding a longitudinal sleeve outwardly from a generally cylindrical shape that has outer surfaces parallel relative to a cylindrical axis of said sleeve to a generally non-cylindrical shape that has outer surfaces that are non-parallel relative to said cylindrical axis of said sleeve.

9. The method of claim 5 wherein expanding said expandable member comprises:
maintaining said expandable member at a static location while advancing said pin member in a direction away from a distal tip of said expandable member.

10. The method of claim 5 wherein forming said tunnel includes forming said tunnel having an entrance and wherein locating said soft tissue replacement includes passing at least a portion of said soft tissue replacement through said entrance.

11. The method of claim 10 wherein locating said soft tissue replacement further includes locating a portion of said soft tissue replacement at a location that extends out of said entrance during said urging of said soft tissue replacement into contact with said bone.

12. The method of claim 5, further comprising inserting biologic material through a passage formed on a proximal end of said expandable member.

13. The method of claim 12 wherein inserting said biologic material further comprises connecting a cannulated shaft between said passage on said expandable member and a delivery device and urging said biologic material from said delivery device through said cannulated shaft and into said passage on said expandable member.

14. A method for securing a soft tissue replacement in a bone tunnel comprising:
forming a tunnel in a bone;
locating the soft tissue replacement in said tunnel;
locating an expandable member into said tunnel having the soft tissue replacement between said expandable member and a bone surface defining said tunnel, wherein said expandable member includes a first outer member and a second inner member extending from said first outer member, said second inner member having a first end communicating with said first outer member and a second end extending from said first outer member;
expanding said expandable member thereby urging said soft tissue replacement into contact with said bone surface, wherein expanding said expandable member includes translating said second inner member relative to said first outer member wherein said first outer member expands outwardly as a result of said translation thereby urging the soft tissue replacement into the bone tunnel;
rotating said second inner member relative to a longitudinal axis of said first outer member; and
removing said second inner member from said first outer member.

15. The method of claim 14 wherein rotating said second inner member comprises rotating a hook portion extending from said distal end of said second inner member from an engaged position with said first outer member into a disengaged position from said first outer member.

16. The method of claim 14 wherein expanding said expandable member comprises:
expanding a longitudinal sleeve outwardly from a generally cylindrical shape that has outer surfaces parallel relative to a cylindrical axis of said first outer member to a generally non-cylindrical shape that has outer surfaces that are non-parallel relative to said cylindrical axis of said first outer member.

17. The method of claim 14 wherein forming said tunnel includes forming said tunnel having an entrance and wherein locating said soft tissue replacement includes passing at least a portion of said soft tissue replacement through said entrance.

18. The method of claim 17 wherein locating said soft tissue replacement further includes locating a portion of said soft tissue replacement at a location that extends out of said entrance during said urging of said soft tissue replacement into contact with said bone.

19. The method of claim 14, further comprising inserting biologic material through a passage formed on a proximal end of said expandable member.

20. The method of claim 19 wherein inserting said biologic material further comprises connecting a cannulated shaft between said passage on said expandable member and a delivery device and urging said biologic material from said delivery device through said cannulated shaft and into said passage on said expandable member.

21. A method for securing a soft tissue replacement in a bone tunnel comprising:
forming a tunnel in a bone;
locating the soft tissue replacement in said tunnel;
locating an expandable member into said tunnel having the soft tissue replacement between said expandable member and a bone surface defining said tunnel, wherein said expandable member includes a first outer member and a second inner member extending from said first outer member, said second inner member having a first end communicating with said first outer member and a second end extending from said first outer member;

expanding said expandable member thereby urging said soft tissue replacement into contact with said bone surface, wherein expanding said expandable member includes translating said second inner member relative to said first outer member wherein said first outer member expands outwardly as a result of said translation thereby urging the soft tissue replacement into the bone tunnel; and maintaining said expandable member at a static location while advancing said second inner member in a direction away from a distal tip of said expandable member.

* * * * *